(12) United States Patent
Truitt

(10) Patent No.: US 7,975,688 B1
(45) Date of Patent: Jul. 12, 2011

(54) VIBRATION REDUCING BLOWER ASSEMBLY MOUNTING

(75) Inventor: Patrick W Truitt, Murrysville, PA (US)

(73) Assignee: RIC Investments, LLC, Wilmington, DE (US)

( * ) Notice: Subject to any disclaimer, the term of this patent is extended or adjusted under 35 U.S.C. 154(b) by 2246 days.

(21) Appl. No.: 10/790,322

(22) Filed: Mar. 1, 2004

Related U.S. Application Data

(60) Provisional application No. 60/454,825, filed on Mar. 14, 2003.

(51) Int. Cl.
*A61M 15/00* (2006.01)
*A61M 16/00* (2006.01)

(52) U.S. Cl. .................................. 128/200.24

(58) Field of Classification Search ............ None
See application file for complete search history.

(56) References Cited

U.S. PATENT DOCUMENTS

| | | | |
|---|---|---|---|
| 5,904,141 A * | 5/1999 | Estes et al. ............... | 128/204.23 |
| 6,216,691 B1 * | 4/2001 | Kenyon et al. ........... | 128/205.18 |
| 6,216,961 B1 | 4/2001 | Kenyon et al. | |
| 6,315,526 B1 | 11/2001 | Jones | |
| 6,511,288 B1 * | 1/2003 | Gatley, Jr. ................... | 415/206 |
| 6,926,503 B2 * | 8/2005 | McGee et al. ............... | 417/363 |
| 2003/0042392 A1 | 3/2003 | Mann | |

* cited by examiner

*Primary Examiner* — Nicholas D Lucchesi
*Assistant Examiner* — Pritesh Patel
(74) *Attorney, Agent, or Firm* — Michael W. Haas

(57) ABSTRACT

A medical device, such as a respiratory treatment device, includes a passive acoustic noise reduction system in the form of a vibration reducing blower assembly isolation mount. The device includes a housing, a blower assembly mounted therein, a patient circuit coupled to the blower assembly, and a noise reducing blower assembly isolation mount. The mount includes a first vibration damping member adjacent one side of the blower assembly spacing the blower assembly from a mounting surface upon which the blower assembly is supported. A securing member positions and holds the blower assembly onto the mounting surface, and a second vibration damping member adjacent an opposite side of the blower assembly spaces the blower assembly from the securing member. The vibration damping members are injection molded thermoplastic elastomeric members.

12 Claims, 4 Drawing Sheets

VIBRATION REDUCING BLOWER ASSEMBLY MOUNTING

CROSS-REFERENCE TO RELATED APPLICATIONS

This application claims priority under 35 U.S.C. §119(e) from provisional U.S. patent application No. 60/454,825 filed Mar. 14, 2003 the contents of which are incorporated herein by reference.

BACKGROUND OF THE INVENTION

1. Field of the Invention

The present invention relates a method and apparatus for vibration reduction in a medical device incorporating a motor and, more particularly, to pressure support system with a vibration-reducing blower assembly mounting.

2. Background Information

Breathable gas delivery devices are used for a variety of respiratory treatments, such as a Continuous Positive Air Pressure (CPAP) treatment of Obstructive Sleep Apnea (OSA). These treatments are often delivered to the patient while the patient, and any bed partners, are sleeping. Consequently, in the field of respiratory treatment devices, minimizing sound emission of the device is of significant concern. Any noise can serve to disrupt the patient's sleep, or the sleep of others, and should be minimized. In addressing this issue, existing respiratory devices have utilized sound insulating materials, e.g., foam, in the housing construction. The insulation and foams of the prior art are reliable methods of reducing noise; however, the use of insulation and foams becomes difficult with smaller product profiles. In other words, as the products are being made smaller, the thickness of the insulation is decreased and the effectiveness of the foam is reduced.

U.S. Pat. No. 6,216,691, which is incorporated herein by reference, discloses a mounting body for a blower assembly of a respiratory device intended to reduce vibration-associated noise of the device. The '691 patent teaches a mounting body formed out of a compliant material mounting the blower assembly to the housing. The compliant material disclosed includes foamed thermosetting plastic and foamed silicone. Further, the body includes a recess of a complementary shape to the blower assembly encapsulating the blower assembly. Additionally, the body is required to have sufficient structural rigidity to perform the mounting function and support the weight of the blower assembly and other associated structure.

SUMMARY OF THE INVENTION

It is an object of the present invention to address the problem of vibration reduction in respiratory treatment devices. It is a further object to provide an apparatus and method for noise reduction that will be applicable to a variety of medical devices. It is a further object of the invention to provide reliable noise reduction utilizing inexpensive proven technology and concepts.

The above problems with the prior art are addressed with a medical device having vibration reduction in accordance with the present invention. Specifically, the invention provides a respiratory treatment device that includes a vibration reducing blower assembly isolation mount. The device includes a housing, a blower assembly mounted therein, a patient circuit coupled to the blower assembly, and a vibration reducing blower assembly isolation mount. The vibration reducing blower assembly isolation mount includes a first vibration damping member that is disposed between the blower assembly and the housing.

In a further embodiment of the present invention, the vibration reducing blower assembly isolation mount includes a second vibration damping members and a securing member. The first vibration damping member is adjacent one side of the blower assembly, spacing the blower assembly from a mounting surface upon which the blower assembly is supported. The securing member positions and holds the blower assembly onto the mounting surface. The second vibration damping member is adjacent an opposite side of the blower assembly spacing the blower assembly from the securing member. The vibration damping members may, preferably, be injection molded thermoplastic elastomeric members.

The invention is not limited solely to respiratory devices but is applicable more broadly to medical devices. The invention, more broadly, is a system for reducing vibration and acoustic noise of a medical device having a housing and a noise source, such as a blower assembly or motor, mounted in the housing. The system effectively isolates the noise or vibration source from the housing. The unique mounting structure allows for easy assembly and maintenance in a low cost structure and which allows for retrofitting of the system into a number of existing medical devices with minimal redesigning.

The invention is particularly well suited for respiratory devices with a blower that delivers pressurized gas to the airway of a patient. In one embodiment of the invention, the apparatus includes a pair of injection molded thermoplastic elastomeric members positioned on opposite sides of the blower assembly, also known as the gas flow generator. One embodiment provides a rigid mounting plate within the housing for supporting the blower assembly, which is held in position by a rigid securing member. The securing member may include a recess for receiving and locating a portion of the blower assembly and one of the injection molded thermoplastic elastomeric members, and at least two attaching legs extending to and fastened to the mounting plate. One embodiment of the invention may further include an injection molded thermoplastic elastomeric tubular coupling between the blower assembly and the patient gas delivery means. Further, the patient gas delivery system may include a valve attached to the mounting plate, wherein injection molded thermoplastic elastomeric members are positioned between the valve and the mounting plate for further vibration reduction.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
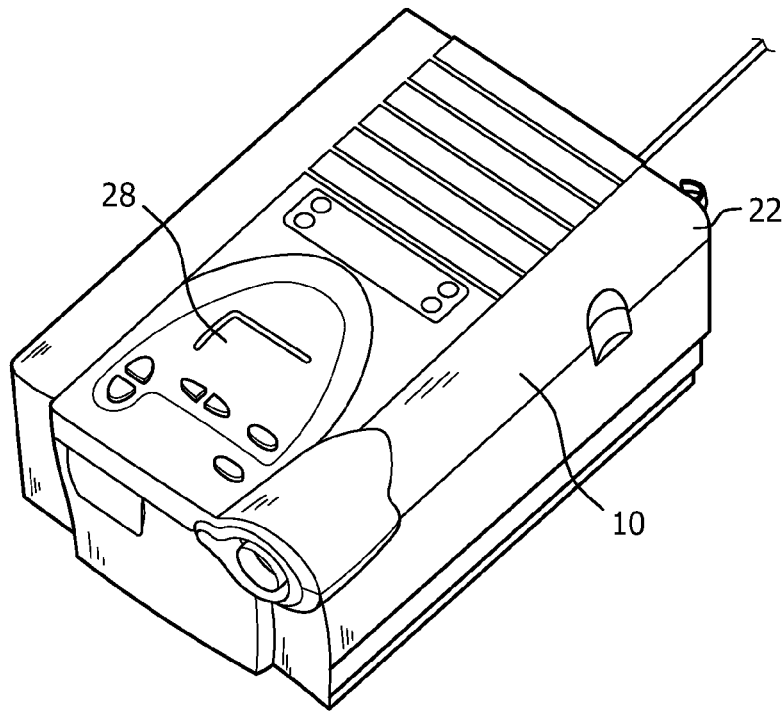
FIG. 1 is a perspective view of a respiratory treatment device including vibration reduction according to the present invention.
Figure 2:
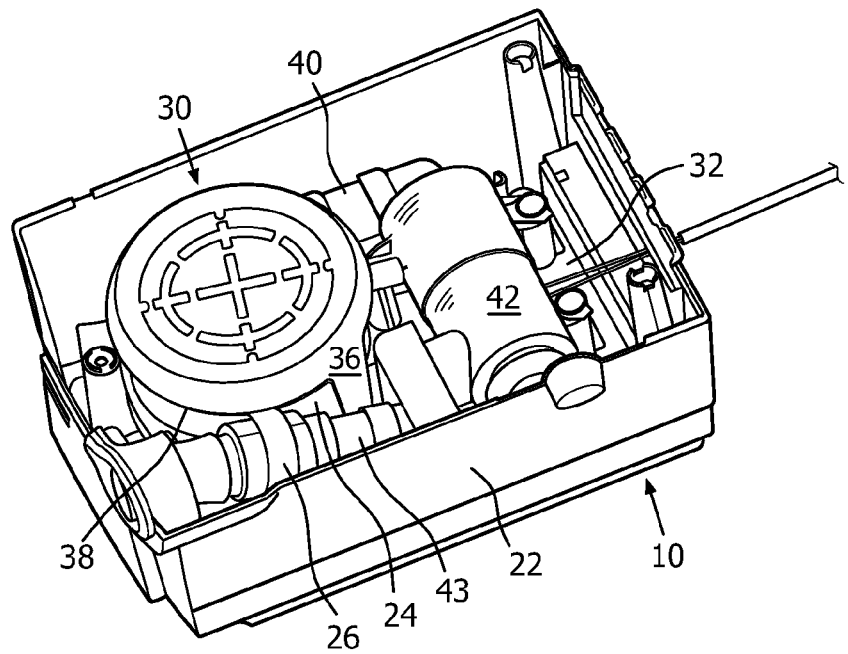
FIG. 2 is a perspective view of the device of FIG. 1 with a portion of the housing removed.
Figure 3:
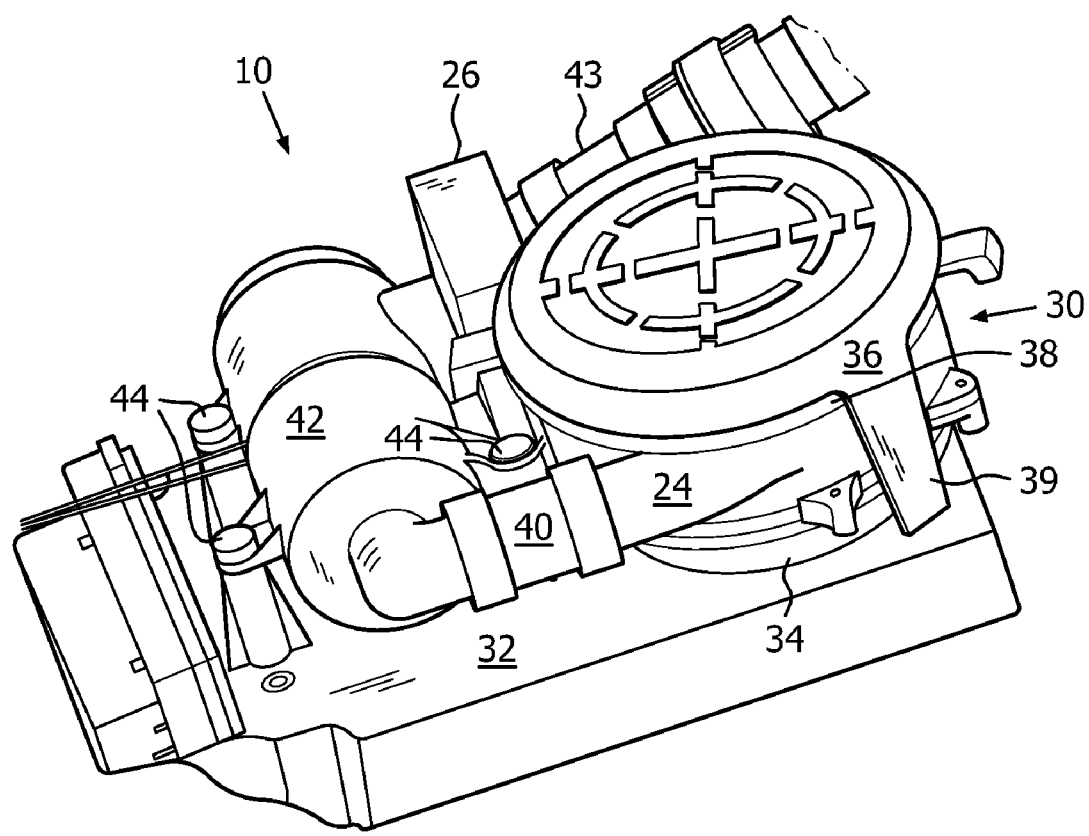
FIG. 3 is a perspective view of the device of FIG. 1 with the housing removed.
Figure 4:
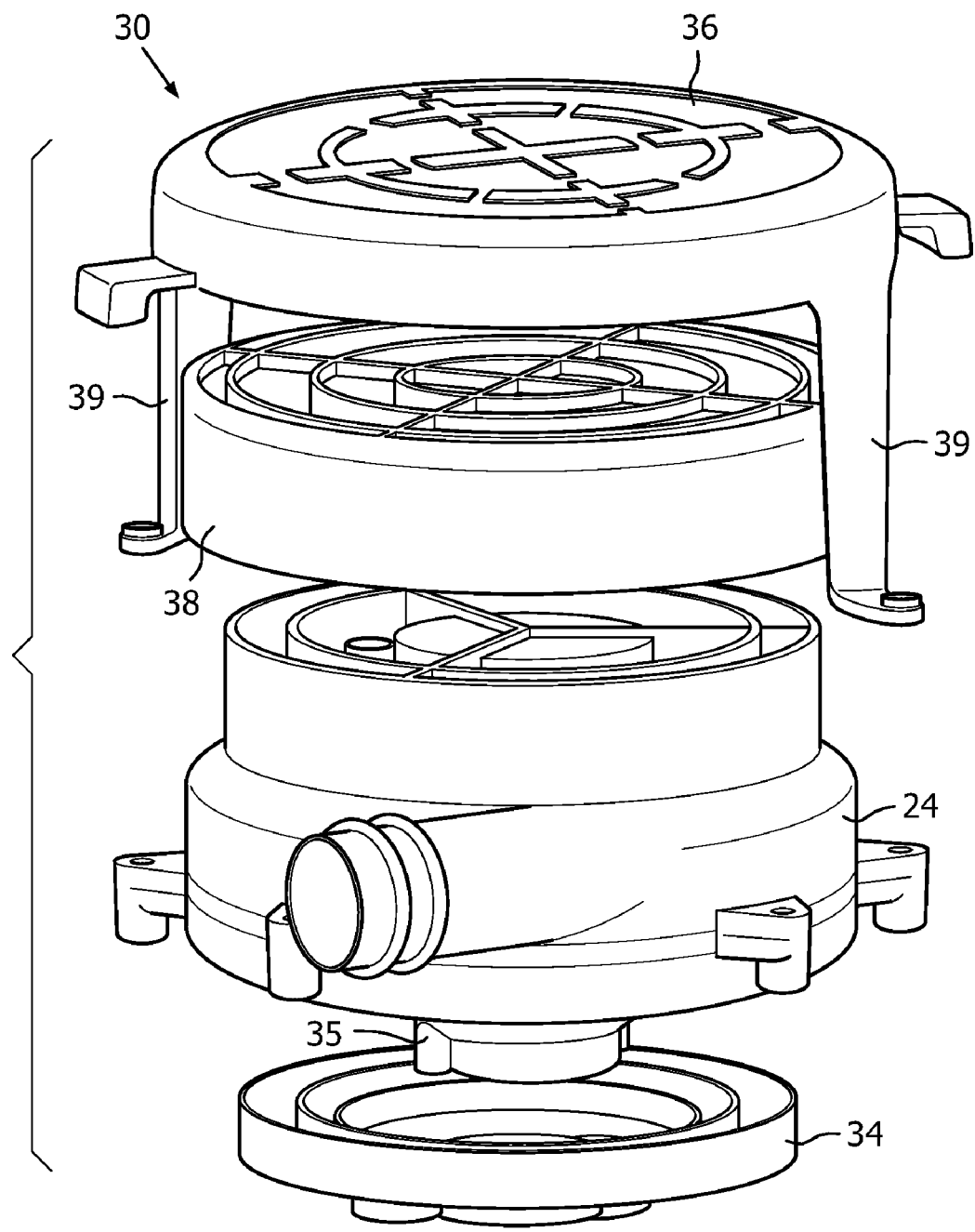
FIG. 4 is an exploded view of the blower assembly isolation mount of FIG. 3.
Figure 5A:
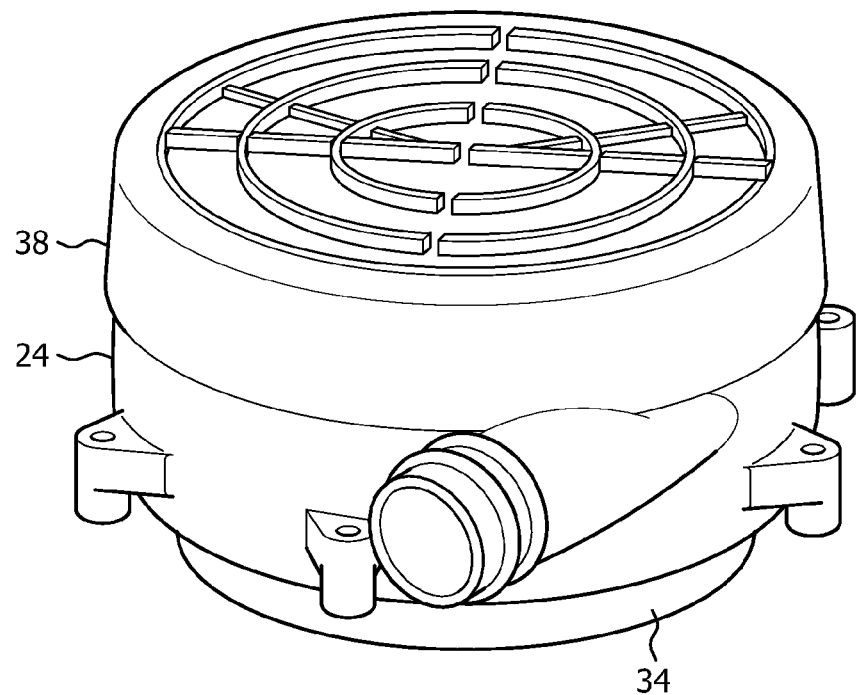
FIGS. 5A and 5B are top and bottom perspective views, respectively, of several components of the blower assembly isolation mount of FIG. 3 in an assembled position.
Figure 5B:
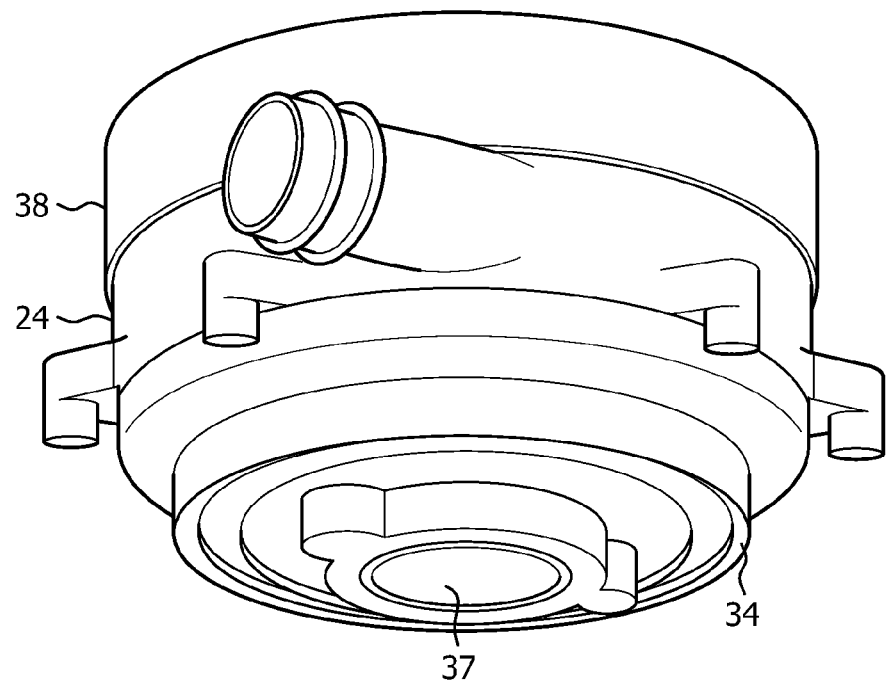

The present invention is illustrated in FIGS. 1-5B. A respiratory treatment device 10, which is also referred to as a pressure support system, is generally for delivering pressurized gas to the airway of a patient (not shown). The respiratory treatment device 10 may be a Positive Air Pressure (PAP) device, a Constant Positive Air Pressure (CPAP) device, a bi-level device that varies the pressure provided to the patient during each inspiratory and expiratory phase, an auto-titration pressure support system that varies the pressure provided to the base based on the monitored condition of the patient, or pressure support systems operating according to conventional pressure support modes, as known in the art. Examples of these types of devices are sold by Respironics, Inc. of Murrysville, Pa., U.S.A.

The apparatus or respiratory treatment device 10 includes a housing 22 with a blower assembly 24, also called a gas flow generator, mounted in housing 22. Blower assembly 24 generates a flow of a pressurized gas. A patient gas delivery circuit 26, referred to more succinctly as a patient circuit, is coupled to blower assembly 24 and to the patient for communicating with and providing the pressurized gas to the airway of a patient. A conventional tubing assembly (not shown) terminating in a patient mask, nose cannula structure or other conventional patient interface device forms the portion of patient gas delivery circuit 26 from housing 22 to the patient, as known in the art. Blower assembly 24 can be generally considered as a gas flow generator means for providing a flow of a pressurized gas and patient circuit 26 can be generally considered as a patient gas delivery means. Controls 28 are provided for operation of blower assembly 24.

Controls 28, blower assembly 24, and patient gas delivery circuit 26 are generally conventional in the art and will not be described in detail herein, e.g. the specifics of the valves, control circuitry, fluid coupling, and the like are not shown or described in detail, but are well known to those in the art.

The key aspect of the present invention is the provision of a blower isolation mounting system 30 in housing 22 for minimizing vibration and associated acoustic noise of blower assembly 24. Housing 22, as is common in the art, is formed of generally rigid injection molded polymers. Housing 22 is required to provide the structural support and structural integrity for respiratory treatment device 10. This function essentially requires the rigid structure. However, a rigid structure easily transmits vibration therethrough. Acoustic noise minimizing system 30 isolates blower assembly 24 from housing 22 to minimize the vibration that is transmitted thereto and thereby minimize the associated noise of respiratory treatment device 10.

Acoustic noise minimizing system 30 includes a rigid mounting plate 32 mounted in and attached to housing 22 for supporting the blower assembly 24. A first vibration damping member 34 is adjacent one side of blower assembly 24 spacing blower assembly 24 from a mounting surface of mounting plate 32 upon which the blower assembly is supported. A securing member 36 positions and holds blower assembly 24 onto the mounting surface of mounting plate 32. A second vibration damping member 38 is adjacent an opposite side of blower assembly 24 spacing the blower assembly from securing member 36.

First and second vibration damping members 34 and 38 are preferably injection molded thermoplastic elastomer, such as a 2.79 durometer rubber compound. Thermoplastic elastomers behave as elastomers, e.g., rubber, at ambient temperature but are thermoplastic, i.e., deformable, at elevated temperatures. Examples include polyisoprene and polyisobutylene. An injection molded thermoplastic elastomer suitable for use in the present invention is the VERSAFLEX CL2000X thermoplastic rubber compound manufactured by GLS corporation of McHenry, Ill. It should be noted that the present invention contemplates that a variety of similar compounds are suitable for use in the present invention. For example, injection molded thermoplastic elastomers with different durometers can be used depending on the magnitude of the vibration isolation desired and the frequency of the vibration to be dampened.

In a typical application, the injection molded thermoplastic elastomer has a durometer in a range of 1-40 on the Shore A scale. It should be noted, however, that if heavier blower assemblies may require higher durometer material to prevent crushing. Other materials suitable for use as first and second vibration damping members 34 and 38 include, but are not limited to silicon, rubber, and foam, so long as the foam can support the weight of the blower assembly without crushing. In short, any vibration dampening material can be used for first and second vibration damping members 34 and 38 so long as the durometer is sufficiently low so as to prevent transmission of vibrations to the blower housing or the mounting plate without being crushed.

The use of injection molded thermoplastic elastomer allows for forming of vibration damping members 34 and 38 in a variety of convenient shapes to conform to blower assembly 24 and to space the blower assembly from securing member 36 and mounting plate 32. For example, note that second vibration damping member 38 includes a recess that receives a portion of blower assembly 24. In addition, a inlet opening 37 is defined in first vibration damping members 34 that is sized and configured to receive an inlet portion 35 of blower assembly 24.

Securing member 36 is a rigid structure generally formed in the same manner as mounting plate 32 and housing 22. Securing member 36 includes a recess for receiving and locating a portion of blower assembly 24 and second vibration damping member 38, and at least two opposed attaching legs 39 extending to and fastened to mounting plate 32. The fastening of securing member 36 to mounting plate 32 may be by conventional fastening means, such as screws or the like. Vibration damping members 34 and 38 isolate and "float" blower assembly 24 from securing member 36 and from mounting plate 32, and ultimately housing 22.

Acoustic noise minimizing system 30 of the invention further includes an injection molded thermoplastic elastomeric tubular coupling 40 between blower assembly 24 and patient gas delivery circuit 26. Pliant coupling 40 further isolates the blower assembly 24.

Additionally, patient gas delivery circuit 26 includes a valve 42 attached to mounting plate 32. The present invention provides for isolation mounts 44 for attaching valve 42 to mounting plate 32. In an exemplary embodiment of the present invention, mounts 44 are injection molded thermoplastic elastomeric members positioned between valve 42 and mounting plate 32. Mounts 44 may take a number of different forms, as will be appreciated by those in the art, provided that the mounts provide a spacing of elastomeric material between valve 42 and mounting plate 32, including any fastening members, e.g., screws. Another compliant coupling 43 can be provided in patient gas delivery circuit 26 between the valve 42 and housing coupling 54.

While the present invention contemplates that couplings 40 and 43, as well as isolation mounts 44, are formed from the same material as first and second vibration damping members 34 and 38, it is to be understood that the present invention contemplates, but does not require, that couplings 40 and 43 and isolation mounts 44 are formed from a higher durometer injection molded thermoplastic elastomer. For example, the present invention contemplates that couplings 40 and 43, in a typically application, have a durometer of 13 on the Shore A scale, and isolation mounts 44 have a durometer of 30 on the Shore A scale. In general, the durometer for couplings 40 and 43, for typical applications, can range from 1-40 on the Shore A scale, and the durometer for isolation mounts 44 can range from 1-40 on the Shore A scale. The durometer for the couplings should be sufficient to provide the coupling function and maintain a pressure seal with the element to which the coupling is connected. The present invention contemplates reinforcing at least a portion of the coupling if lower durometer materials are used to provide the necessary mechanical integrity for the coupling.

In addition, each of the injection molded thermoplastic elastomer members, couplings, and mounts can be formed form compounds with different specific properties. That is, the individual items can have different durometers. In addition, each item can be formed from a combination of materials. For example, as noted above, the coupling can include reinforcements, such as strips or wires inserted into or disposed on the coupling or a portion of the coupling. The present invention also contemplates that the coupling 40 can include the elbow portion of the circuit that connects to valve 42.

Respiratory treatment device 10 provides a quiet device at a relatively low cost. It is designed for easy repair and maintenance. Furthermore, the design can be easily retrofitted to existing housing structures in other respiratory and other medical devices. The use of the elastomeric material avoids the difficulties with foam noise attenuation techniques of the prior art that required a certain foam thickness for desired effectiveness.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An apparatus for delivering pressurized gas to the airway of a patient, the apparatus comprising:
    a housing;
    a mounting surface disposed on the housing;
    a blower assembly operatively coupled to the mounting surface and adapted to generate a flow of a pressurized gas;
    a patient circuit coupled to the blower assembly and adapted to communicate the flow of gas to an airway of a patient;
    a first vibration damping member disposed between a first side of the blower assembly and the mounting surface upon which the blower assembly is supported, the first vibration damping member being in contact with each of the first side of the blower assembly and the mounting surface so as to space the blower assembly from the mounting surface;
    a securing member positioning and holding the blower assembly onto the mounting surface, wherein the securing member is a rigid member that includes:
        a recess for receiving and locating a portion of the blower assembly and the second vibration damping member, and
        at least two attaching legs extending to and fastened to the mounting surface; and
    a second vibration damping member disposed between a second side of the blower assembly opposite the first side and the securing member, the second vibration damping member being in contact with each of the second side of the blower assembly and the securing member so as to space the blower assembly from the securing member.

2. The apparatus of claim 1, wherein the second vibration damping member includes a recess receiving a portion of the blower assembly.

3. The apparatus of claim 2, wherein the mounting surface is on a rigid mounting plate secured to the housing.

4. The apparatus of claim 3, further comprising an injection molded thermoplastic elastomeric tubular coupling between the blower assembly and the patient circuit.

5. The apparatus of claim 4, further comprising a valve attached to the mounting plate in fluid communication with the patient circuit, and an additional injection molded thermoplastic elastomeric member is positioned between the valve and the mounting plate.

6. A vibration isolation mounting system for a blower assembly mounted in a housing, the system comprising:
    a mounting surface supporting the blower assembly within a housing;
    a first vibration damping member disposed between a first side of the blower assembly and the mounting surface, the first vibration damping member being in contact with at least a portion of each of the first side of the blower assembly and the mounting surface such that the blower assembly is spaced apart from the mounting surface by the first vibration damping member;
    a securing member positioning and holding the blower assembly to the mounting surface, wherein the securing member is a rigid member that includes:
        a recess receiving and locating a portion of the blower assembly and the second vibration damping member, and
        at least two attaching legs extending to and fastened to the mounting surface; and
    a second vibration damping member disposed between a second side of the blower assembly opposite the first side and the securing member, the second vibration damping member being in contact with at least a portion of each of the second side of the blower assembly and the securing member such that the blower assembly is spaced apart from the securing member.

7. The system of claim 6, wherein the first and the second vibration damping members are injection molded thermoplastic elastomeric members.

8. The system of claim 7, wherein the mounting surface is on a rigid mounting plate secured to the housing.

9. The system of claim 8, further comprising an injection molded thermoplastic elastomeric coupling attached to the blower assembly.

10. The system of claim 7, wherein the thermoplastic elastomeric members are formed of a rubber compound of about 2.79 durometers.

11. The system of claim 7, further comprising an injection molded thermoplastic elastomeric tubular coupling attached to the blower assembly, wherein the tubular coupling includes a pair of end sections and an intermediate section with a wall thickness less than that of the end sections.

12. The system of claim 7, wherein at least one of the vibration damping members includes a recess for receiving a portion of the blower assembly.

* * * * *